(12) United States Patent
Samie et al.

(10) Patent No.: US 11,512,109 B2
(45) Date of Patent: Nov. 29, 2022

(54) **METHOD FOR EXTRACTION OF POWDERED SILK FIBROIN FROM *BOMBYX MORI* COCOONS USING AQUEOUS SOLUTION OF BASIC IONIC LIQUID**

(71) Applicant: COMSATS UNIVERSITY ISLAMABAD, Islamabad (PK)

(72) Inventors: Muhammad Samie, Lahore (PK); Nawshad Muhammad, Lahore (PK); Hamad Khalid, Lahore (PK); Ather Farooq Khan, Lahore (PK)

(73) Assignee: COMSATS UNIVERSITY ISLAMABAD, Islamabad (PK)

( * ) Notice: Subject to any disclaimer, the term of this patent is extended or adjusted under 35 U.S.C. 154(b) by 422 days.

(21) Appl. No.: 16/844,070

(22) Filed: Apr. 9, 2020

(65) Prior Publication Data

US 2020/0331961 A1    Oct. 22, 2020

(30) Foreign Application Priority Data

Apr. 18, 2019  (PK) ..................................... 239/2019

(51) Int. Cl.
| | | |
|---|---|---|
| *C07K 14/00* | (2006.01) | |
| *C07K 1/30* | (2006.01) | |
| *C07K 14/435* | (2006.01) | |

(52) U.S. Cl.
CPC ........ *C07K 1/303* (2013.01); *C07K 14/43586* (2013.01)

(58) Field of Classification Search
CPC .......................... C07K 1/303; C07K 14/43586
See application file for complete search history.

(56) References Cited

PUBLICATIONS

Periera et al. ACS Omega 2018, 3, 9, 10811-10822.*
Gupta et al. Langmuir 2007, 23, 3, 1315-1319.*

* cited by examiner

*Primary Examiner* — Jeanette M Lieb
(74) *Attorney, Agent, or Firm* — Oliff PLC

(57) ABSTRACT

A method is provided for extraction of fine silk fibroin powder from *Bombyx mori* silk cocoons. The conventional method of silk processing includes dissolution of the degummed silk fibers in some strong salt solutions followed by a dialysis step. The earlier reported strong salt solutions have either associated environment issues or lower dissolution ability for silk. However, the provided method includes degumming silk cocoons, drying and cutting the degummed silk fibers, mixing the fibers with an ionic liquid, stirring the mixture, regeneration of silk from the mixture with the help of an anti-solvent followed by centrifugation, drying the precipitated silk and finally obtaining a fine powder of silk.

15 Claims, 5 Drawing Sheets

METHOD FOR EXTRACTION OF POWDERED SILK FIBROIN FROM *BOMBYX MORI* COCOONS USING AQUEOUS SOLUTION OF BASIC IONIC LIQUID

BACKGROUND

The disclosed embodiments pertain a method to extract silk from *Bombyx mori* cocoons by employing basic ionic liquids.

Silk is a natural protein-based polymer produced by various insect species among which domesticated mulberry silkworm (*Bombyx mori*) is the most common. Silk fibroin obtained from cocoons produced by *Bombyx mori* has been used for centuries by the textile industry. However, it has got too much attention in the previous few decades for its use as a biomaterial which was initially limited to production of sutures and then to fabricating biomedical materials for various applications. Silk in its natural form consists of two proteins: Fibroin and Sericin. Fibroin is the structural component and consists of a high (MW: 390 kDa) and low (MW: 26 kDa) molecular weight macromolecular chains with specific conformations both joined by a disulfide bond. The fibroin is surrounded by the gelatinous water-soluble protein sericin. To dissolve the fibroin, disruption of the bridging bonds between the two chains is required. For this purpose, aqueous inorganic salt solutions and concentrated acid solutions are usually used because of their ability to disrupt hydrogen bonding.

For biomedical applications, silk is mostly used in the form of regenerated solution, but the short half-life of about a week is a factor that hinders the production of valuable products from this polymer. Another problem associated with the use of inorganic salt solutions is the degradation of protein during the process. However, an alternative way to use a silk solution for a long time is to freeze dry the regenerated solution and reconstitute in some other organic solvent like 1,1,1,3,3,3-hexafluoro-2-propanol (HFIP), hexafluoroacetone (HFA) and anhydrous trifluoroacetone (TFA). On the other hand, these solvents are expensive, toxic and strongly corrosive which forced researchers to look for alternate options. For this purpose, strong acid solutions were studied, and primarily formic acid solution (98%) and phosphoric acid solution were explored. However, the disruption of the peptide bond and denaturation of proteins still remained a major concern while these solutions also failed to be used for prolonged period of time.

Recently ionic liquids (ILs) have emerged as an attractive class of solvents for the solubility of various natural compounds. The solubility of natural fibers using ionic liquids is providing new avenues in terms of selective extraction, regeneration and material synthesis. To date, ionic liquids for the dissolution of natural fibers are mostly based on the imidazolium cation with chloride or acetate anions as per their ability to disrupt the hydrogen bonding. Here, the regeneration of silk into powder is accomplished using one of the ionic liquids choline hydroxide and tetrabutylphosphonium hydroxide. The significance of using these ionic liquids lies in the relatively mild conditions used for processing and cost efficiency. The silk regenerated after treatment with these ionic liquids exhibit almost similar properties to the native silk fibroin; therefore no further processing is required.

SUMMARY

A novel and simple method for the regeneration of silk fibroin from silk cocoons is described according to the disclosed embodiments. Basic ionic liquids (tetrabutylphosphonium hydroxide and choline hydroxide) belonging to the green class of solvents were used. The process was carried out in a time and energy efficient manner under mild conditions of temperature and resulted in the regeneration of a handsome amount of silk powder from original silk fibroin, which may find applications in biomaterial fabrication. This process is a valuable addition to the field of green chemistry where all the products of the reaction are environmentally friendly and the ionic liquid can be recovered and refined with little or no change in the activity and used for further applications.

BRIEF DESCRIPTION OF THE DRAWINGS

Other features and advantages of the invention will become apparent from the following description of some forms of embodiments of the invention, given as nonlimiting examples, with the help of the appended diagrams illustrated in the attached drawings, in which.

DETAILED DESCRIPTION OF EMBODIMENTS

The following illustration of the provided method for regeneration of silk powder from raw silk cocoons is based upon surprising findings that silk can be reproduced in a safe, time and cost-efficient way without altering the properties of its basic structure according to the disclosed embodiments.

The disclosed embodiments relate to a method of extraction of silk fibroin; a potential biomaterial from *Bombyx Mori* silk cocoons. The embodiments introduce a novel process to regenerate silk from raw silk cocoons using a class of solvents called ionic liquids. Being an abundant material obtained from a natural source, silk is a safe and economical polymer. The regeneration of silk is carried out by utilizing the principles of green (environmentally friendly) chemistry using basic ionic liquids. The beauty of using an ionic liquid is that it can be easily recovered and used again after the extraction is carried out. Another advantage of this method is the short processing time under very mild conditions of temperature which enables the silk fibroin to retain its basic structure without the production of any waste material. Therefore, the disclosed embodiments afford a cost effective, yield effective, time effective and eco-friendly process of silk fibroin extraction.

Figure 1:
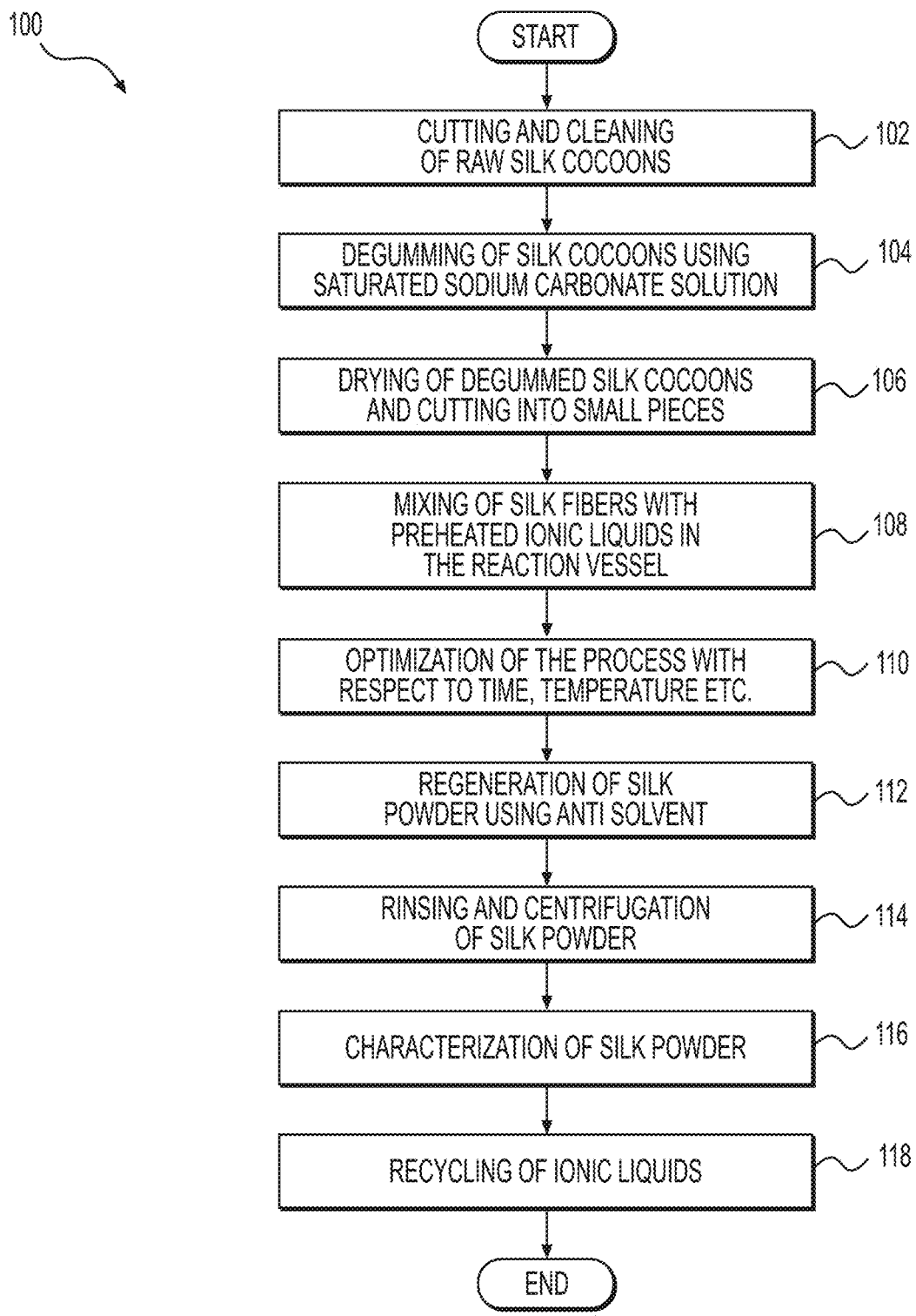
FIG. 1 is a flow chart illustrating the steps involved in the regeneration of silk fibroin from raw silk cocoons using basic ionic liquids according to the disclosed embodiments.

FIG. 1 illustrates a process 100 of extraction of silk fibroin from degummed silk fibers employing basic ionic liquids based on a choline cation and hydroxyl anion according to the disclosed embodiments. Silk fibroin was obtained locally.

The method starts from the start box. The start box represents the start point of a regeneration process according to the disclosed embodiments.

Block 102 provides the first step of cutting the raw silk cocoons and removing the dead larvae and other contamination from cocoons. The cutting of cocoons was carried out using a sharp scissor which helps in the degumming process. The larvae producing the silk resides inside the cocoon; therefore it is required to cut the cocoon to remove any debris and use clean cocoons for degumming.

Block 104 gives a method of degumming where the sericin part is removed by heating at 100° C. using a solution of sodium carbonate for 30 min and then washing three (3) times with deionized water to completely remove the sericin.

Block 106 represents the drying step that is carried out for the degummed fibers. The fibers were placed on a piece of aluminum foil and dried overnight in a hot air oven at 37° C. After that the fibers were cut into small pieces using a sharp scissor.

Block 108 is the method of mixing the small pieces of silk fibers with ionic liquids. The ionic liquid was added first to the reaction vessel and heated up to the desired temperature followed by the addition of silk fibers with continuous stirring to avoid splashing. The method involves heating the reaction mixture in a sand bath placed on a hotplate previously maintained at a constant temperature and standard atmospheric pressure.

Block 110 provides information for optimizing the dissolution process with respect of sample loading, range of temperature, range of pressure, treatment time, stirring speed etc.

Block 112 provides a method for regeneration of the silk powder. After treatment, the sample is cooled down to room temperature followed by adding the anti-solvent and stirring for 10-15 min to precipitate out the dissolved silk completely.

Block 114 represents a method of regeneration and purification of dissolved silk by washing and centrifugation several times with the rinse solvent (mostly anti-solvent) at 10,000 rpm to remove even small traces of ionic liquid from the regenerated silk that is precipitated out.

Block 116 provides a method for characterization of regenerated silk using Fourier-transform infrared spectroscopy (FTIR), Scanning Electron Microscope (SEM), X-ray powder diffraction (XRD) and Thermogravimetric analyzer (TGA) analysis Block 118 is the process of recovery of ionic liquid from the reaction mixture where all the supernatants after every wash are combined and subjected to a rotary evaporator for anti-solvent separation. The supernatant is a mixture of methanol and ionic liquid which is recycled using a rotary evaporator by removing all the rinse solvent, leaving behind pure ionic liquid which may be used again with little or no change in activity. The method may end at the end box.

Ionic liquids possess the potential to dissolve a number of natural fibers. On the basis of cation and anions, these salts have the ability to break hydrogen bonding which results in dissolution. The ionic liquids used may be choline hydroxide or tetrabutylphosphonium hydroxide, for example.

Examples 1-6 demonstrate the method of extraction where a single factor was changed keeping others constant to optimize the dissolution and recovery process. Example 1 demonstrates a generalized method of extraction of silk using one of the ionic liquids (choline hydroxide or tetrabutylphosphonium hydroxide). Example 2 demonstrates the dissolution ability of ionic liquid with respect to a 5-25 wt. % silk sample. Example 3 is presenting the method of silk regeneration using ionic liquid choline hydroxide at 300 rpm for 2 hr at various reaction temperatures ranging 40-60° C. Example 4 is presenting the method of silk regeneration using ionic liquid choline hydroxide at 200 rpm at 40° C. for many treatment times ranging 0.5-2 hours. Example 5 is presenting the method of silk regeneration using ionic liquid choline hydroxide at different magnetic stirring rates ranging 100-300 rpm for 2 hr at 50° C. Example 6 is presenting the method of silk regeneration using ionic liquid choline hydroxide at 200 rpm for 2 hr at 50° C. in which different anti-solvents were used to precipitate the dissolved silk efficiently.

Example 1

Degummed silk fibers were cut into small pieces with the help of a sharp scissor. The ionic liquid—either choline hydroxide (46 wt. % in $H_2O$) or tetrabutylphosphonium hydroxide (40 wt. % in $H_2O$)—was added to the reaction vessel under controlled conditions and maintained at the desired temperature. The silk was then charged into the reaction vessel, stirred and heated for a known period of time. After treatment, anti-solvent was added and stirring continued for an additional 10 min. The precipitated silk was then collected by centrifugation, washed several times with anti-solvent, filtered and dried in an oven at 50° C.

Example 2

Degummed silk fibers were cut into small pieces with the help of a sharp scissor. Choline hydroxide (46 wt. % in $H_2O$) ionic liquid was added to the reaction vessel under controlled conditions and maintained at the desired temperature. The silk was then charged into the reaction vessel containing the ionic liquid until completely dissolved with magnetic stirring and heating for a known period. The amount of silk in the dissolved silk samples ranged from 5-25 wt. %. After treatment, anti-solvent was added and stirring continued for an additional 10 min. The precipitated silk was then collected by centrifugation, washed several times with anti-solvent, filtered and dried in an oven at 50° C.

Example 3

Degummed silk fibers were cut into small pieces with the help of a sharp scissor. Choline hydroxide (46 wt. % in $H_2O$) ionic liquid was added to the reaction vessel under controlled conditions and maintained at the desired temperature. The silk was then charged (25 wt. %) into the reaction vessel until completely dissolved with magnetic stirring and heating at 40-60° C., for example 40, 50, 60° C., for a known period. After treatment, anti-solvent was added and stirring continued for an additional 10 min. The precipitated silk was then collected by centrifugation, washed several times with anti-solvent, filtered and dried in an oven at 50° C.

Example 4

Degummed silk fibers were cut into small pieces with the help of a sharp scissor. Choline hydroxide (46 wt. % in $H_2O$) ionic liquid was added to the reaction vessel under controlled conditions and maintained at the desired temperature. The silk was then charged (25 wt. %) into the reaction vessel until completely dissolved with magnetic stirring and heating at 50° C. for 0.5-2 hours, for example 0.5-hour, 1 hour, 1.5 hours and 2 hours. After treatment, anti-solvent was added and stirring continued for an additional 10 min. The precipitated silk was then collected by centrifugation, washed several times with anti-solvent, filtered and dried in an oven at 50° C.

Example 5

Degummed silk fibers were cut into small pieces with the help of a sharp scissor. Choline hydroxide (46 wt. % in $H_2O$) ionic liquid was added to the reaction vessel under controlled conditions and maintained at the desired temperature. The silk was then charged (25 wt. %) into the reaction vessel until completely dissolved with magnetic stirring at a stirring rate ranging from 100-300 rpm, for example at 100 rpm, 200 rpm and 300 rpm, and heating at 50° C. for 2 hours. After treatment, anti-solvent was added and stirring continued for an additional 10 min. The precipitated silk was then collected by centrifugation, washed several times with anti-solvent, filtered and dried in an oven at 50° C.

Example 6

Degummed silk fibers were cut into small pieces with the help of a sharp scissor. Choline hydroxide (46 wt. % in $H_2O$) ionic liquid was added to the reaction vessel under controlled conditions and maintained at the desired temperature. The silk was then charged (25 wt. %) into the reaction vessel until completely dissolved with magnetic stirring at 200 rpm, and heating at 50° C. for 2 hours. After treatment, anti-solvent was added and stirring continued for an additional 10 min. The anti-solvent used was methanol, water or acetonitrile, for example. The precipitated silk was then collected by centrifugation, washed several times with anti-solvent, filtered and dried in an oven at 50° C.

The regenerated silk was subjected to characterizations like Scanning electron microscopy (SEM), Fourier transform infrared spectroscopy (FTIR), X-ray diffraction (XRD) and Thermogravimetric analysis (TGA).

Scanning Electron Microscopy (SEM)

Figures 2A, 2B, 2C:
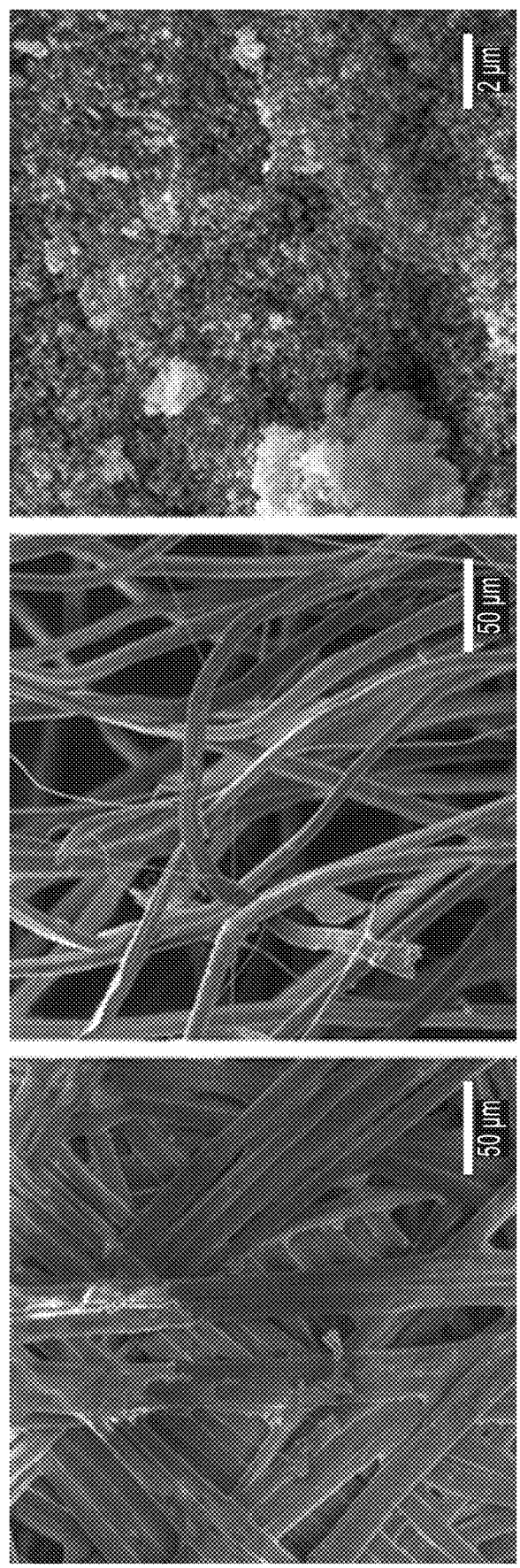
FIGS. 2A-2C are scanning electron micrographs of native silk fibers coated with sericin before degumming (FIG. 2A), dried silk fibers obtained after pre-treatment with sodium carbonate solution (FIG. 2B) and regenerated silk fibroin after treatment with an ionic liquid (FIG. 2C).

From the SEM image, it is evident that the silk has been successfully regenerated in nano powder form. FIG. 2A shows that the silk fibers before degumming (raw cocoon) were stuck tightly to each other with the help of sericin protein. This sericin provides only the adhesive properties and is removed completely during the degumming process, exposing the fibroin protein which is to be used for further applications. The individual silk fibers can be seen in FIG. 2B where the fibroin filaments are completely separated from each other with intact surface morphology. The purpose of using a basic ionic liquid was to disrupt the structure and dissolve the fibroin protein completely. The crystalline structure of regenerated silk powder can be seen in FIG. 2C.

Fourier Transform Infrared Spectroscopy (FT-IR)

Figure 3:
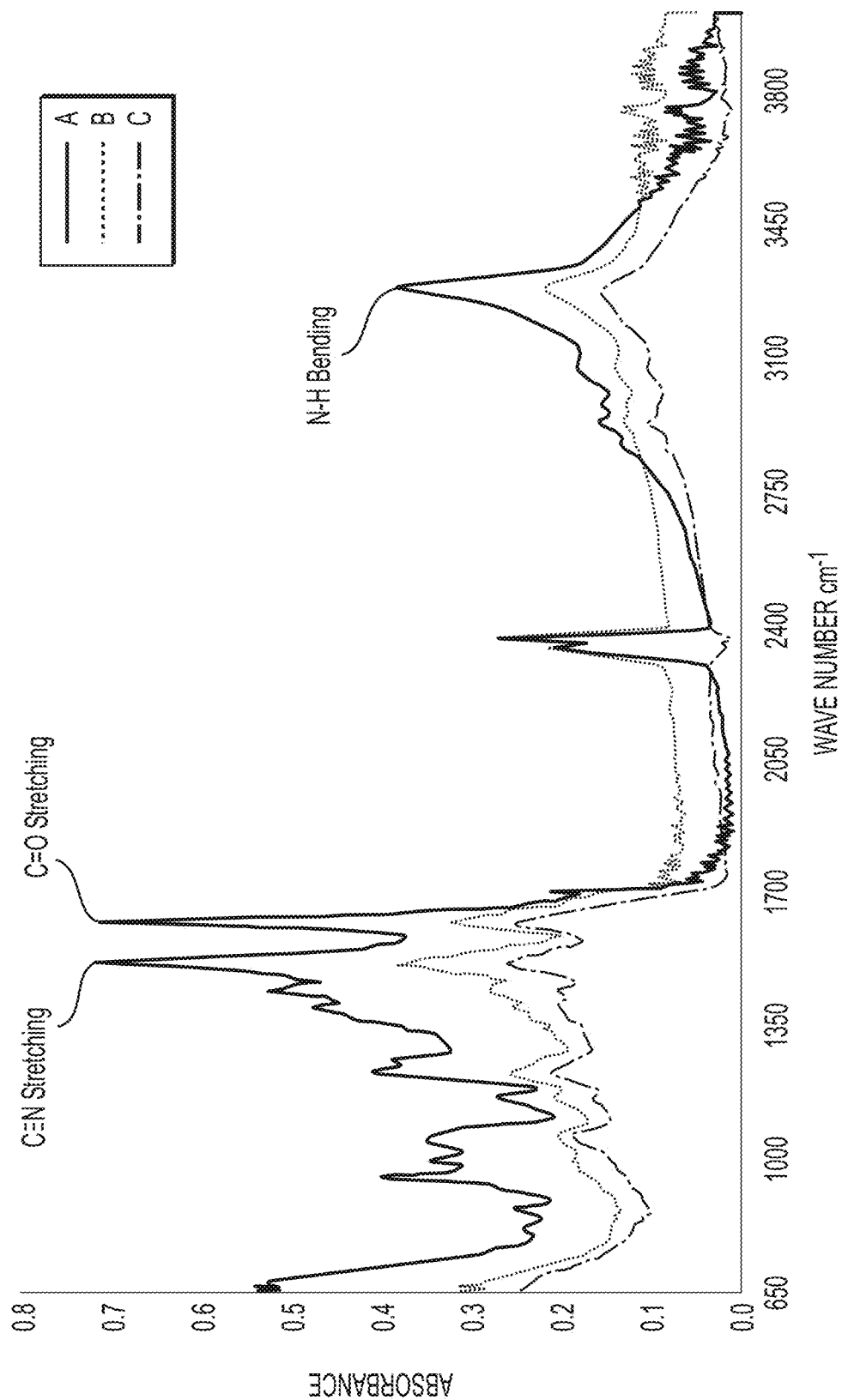
FIG. 3 shows the Fourier transform infrared spectrum of regenerated silk fibroin after treatment with basic ionic liquids (A), degummed silk fibers after pre-treatment with saturated sodium carbonate solution (B) and raw silk cocoons before degumming (C).

The FTIR spectrum of silk cocoons, degummed nanofibers and regenerated silk powder are shown in FIG. 3. The appearance of a peak at 1622 in the spectrum of pure cocoon and degummed silk fibers is attributed to amide I (C=O stretching vibration, β-sheet) which appears sharp (1620) and slightly shifted to the left in the case of regenerated silk. This band seems to be stable and relatively reflects the tyrosine contents. The amide II peak (C≡N stretching and N—H bending, β-sheet) appeared at 1513 which is also shifted to 1508 in the case of regenerated silk. However, this slight change in peak shift is not an indicator of any structural change. This also reveals that there is no or weak molecular interactions between the two fibroin chains. The appearance of amine III peak at 1235 was also attributed to a 0-sheet structure but with certain amount of a random coil structure. A strong and intense amide A band was observed at 3282 (β-sheet) indicating N—H bending. In the case of powder, the increase in peak intensity is ascribed to increased surface area that resulted in deep penetration and exposure of functional groups.

X-Ray Diffraction (XRD)

Figure 4:
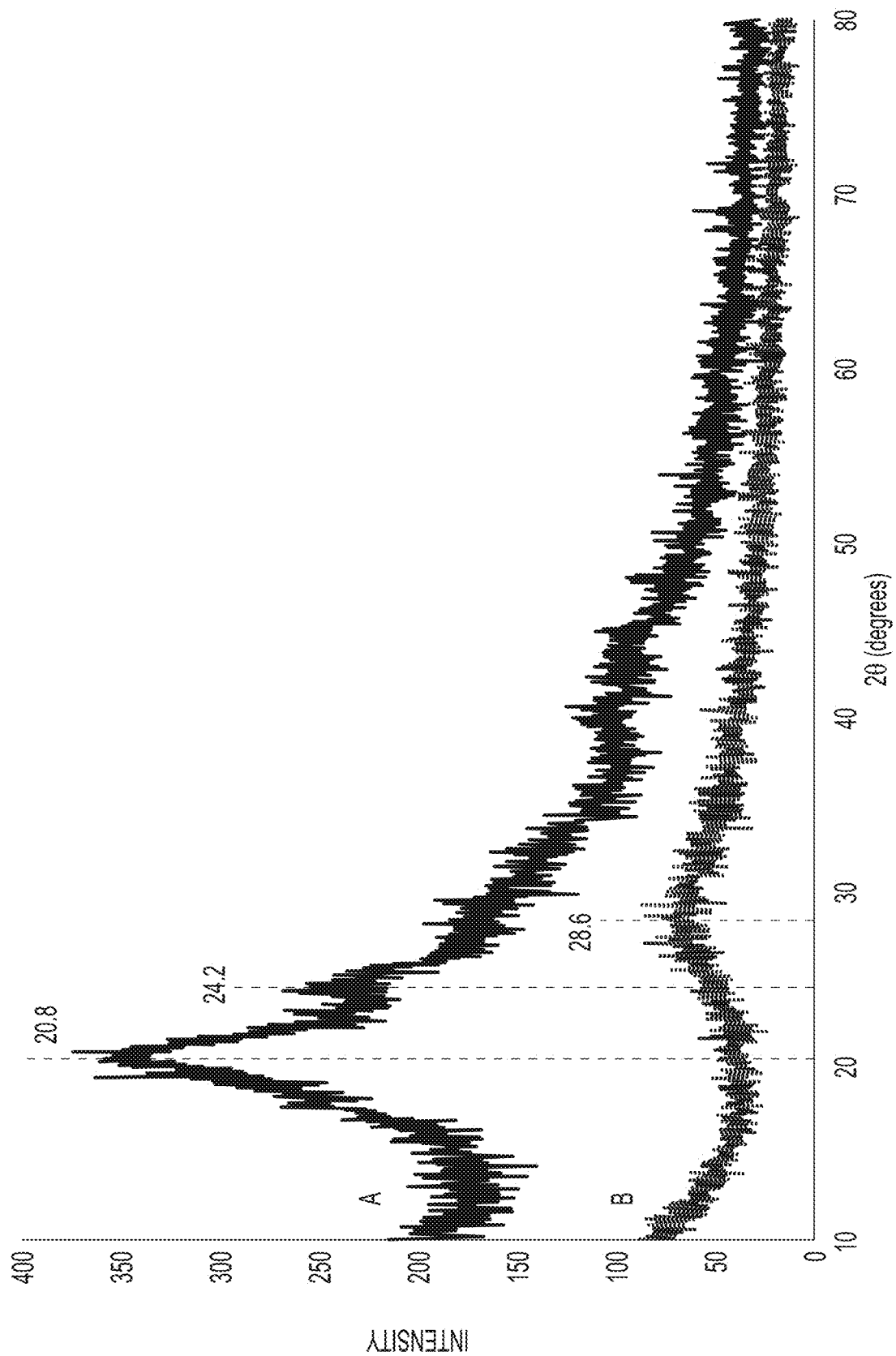
FIG. 4 represents the X-ray diffraction analysis of an original silk cocoon (A) and regenerated silk fibroin after treatment with basic ionic liquids (B).

XRD analysis is an excellent method to investigate the crystalline nature of treated and untreated silk fibroin. The XRD data chart in FIG. 4 shows the appearance of peaks at a 2θ value of 20.8° and 24.2° with an increased chart area corresponding to a β-sheet (silk II) in case of native silk (untreated) (B) as compared to the regenerated silk fibroin where the peak appears at a 2θ value of 28.6° with a smaller area (A) which indicates that the crystalline nature of silk fibroin is completely changed.

Thermogravimetric Analysis (TGA)

Figure 5:
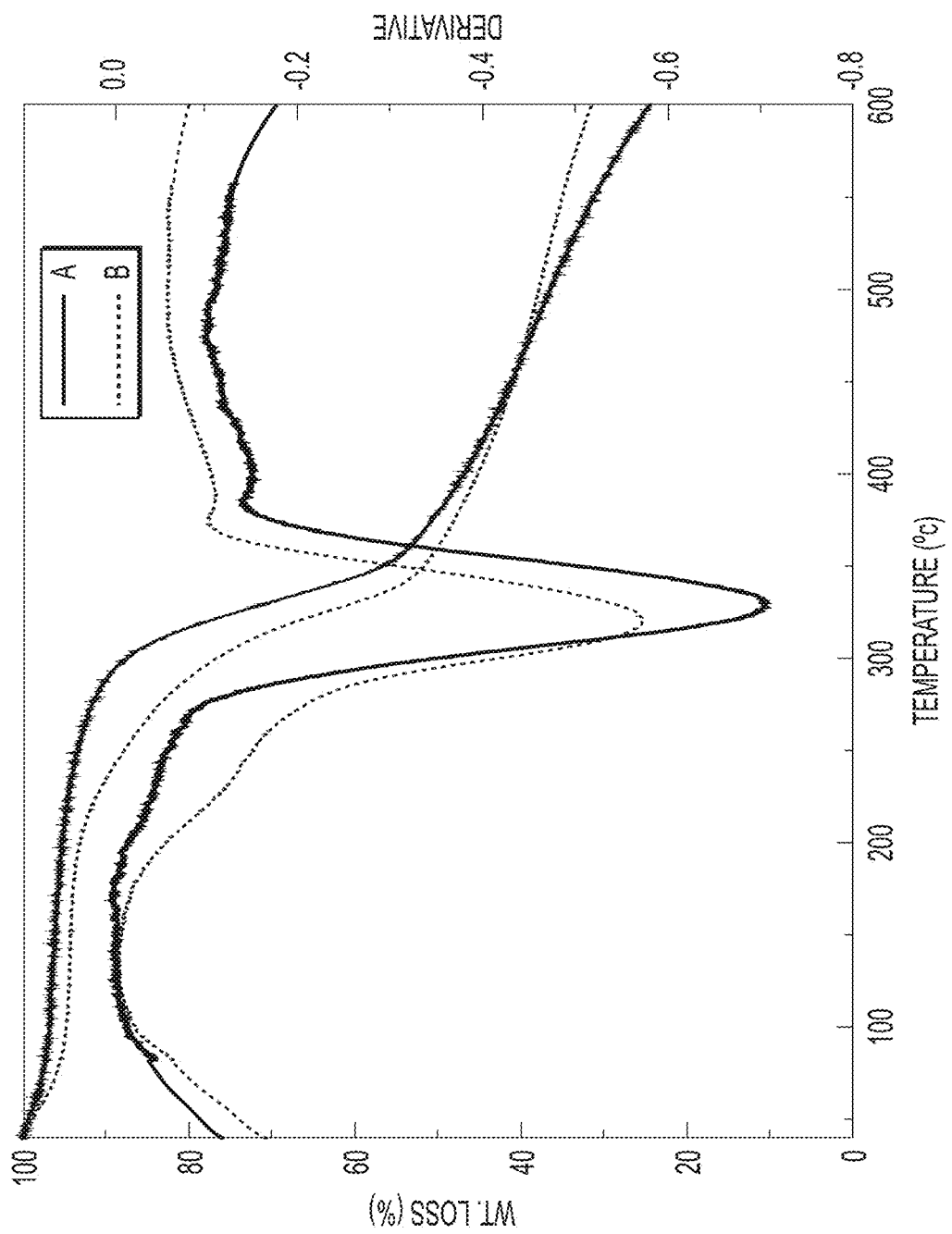
FIG. 5 is the thermogravimetric analysis of degummed silk fibers after pre-treatment with sodium carbonate solution (A) and regenerated silk fibroin after treatment with a basic ionic liquid in accordance with the disclosed embodiments (B).

The thermogravimetric curves of degummed and regenerated silk fibroin after heating up to 600° C. are shown in FIG. 5. The weight decrease behavior in TGA curves can be divided into three distinct regions. The $1^{st}$ region displayed a slow weight loss for degummed silk fibers up to 300° C., whereas the regenerated silk fibroin displayed a slight increase in weight loss after 200° C. The $2^{nd}$ region (300° C.-350° C.) displayed a rapid increase in weight loss where most of the peptide bonds are broken and reduction in intermolecular interactions occurred. The $3^{rd}$ region starting from 350° C. onward displayed a slow and continuous decomposition, however at a slower rate. Overall the degummed silk fibroin has shown a higher thermal stability and increase in total decomposition, whereas in the case of regenerated silk fibroin, a slight decrease in thermal stability and decrease in total decomposition was noted. It is likely that the impurities that interfere with the thermal stability are washed away during the dissolution process. Moreover, it is also found that the degummed silk fibroin exhibited maximum degradation at 328° C. while regenerated silk fibroin showed maximum degradation at 320° C. The total char contents left after complete analysis for degummed silk fibers and regenerated silk fibroin were 25 wt % and 32 wt % respectively.

What is claimed is:

1. A process comprising:
dissolving degummed silk fibers in an ionic liquid to prepare a mixture wherein the ionic liquid comprises choline hydroxide or tetrabutylphosphonium hydroxide;
heating and stirring the prepared mixture;
cooling the heated mixture; and
adding an anti-solvent to the cooled mixture to precipitate silk fibroin.

2. The process of claim 1, wherein the anti-solvent is an organic solvent.

3. The process of claim 1, wherein the anti-solvent is methanol, water, or acetonitrile.

4. The process of claim 1, wherein the anti-solvent is methanol.

5. The process of claim 1, wherein the concentration of degummed silk fibers dissolved in the ionic liquid is up to 25 wt. % of the ionic liquid.

6. The process of claim 1, wherein the heating is performed at a temperature ranging from 40° C. to 60° C.

7. The process of claim 6, wherein the heating is performed at a temperature of 50° C.

8. The process of claim 1, wherein the heating is performed for 0.5-2 hours.

9. The process of claim 1, wherein the stirring is performed at stirring rate in the range of 100-300 rpm.

10. The process of claim 1, wherein the heating is performed under pressure.

11. The process of claim 10, wherein the pressure is standard atmospheric pressure.

12. The process of claim 1, wherein the heated mixture is cooled to room temperature.

13. The process of claim 1, further comprising centrifuging the combined anti-solvent and cooled mixture at 5000-15000 rpm.

14. The process of claim 13, wherein the centrifugation is performed at 10000 rpm.

15. The process of claim 1, wherein the precipitated silk fibroin is in the form of a powder.

* * * * *